United States Patent
Takakura et al.

(10) Patent No.: US 9,090,571 B2
(45) Date of Patent: Jul. 28, 2015

(54) MEGLUMINE SALT OF 6-FLUORO-3-HYDROXY-2-PYRAZINE CARBOXAMIDE

(71) Applicant: TOYAMA CHEMICAL CO., LTD., Tokyo (JP)

(72) Inventors: Keiko Takakura, Toyama (JP); Namika Nakamatsu, Toyama (JP); Sakiko Takeshima, Toyama (JP); Takayoshi Nakashima, Toyama (JP)

(73) Assignee: TOYAMA CHEMICAL CO., LTD., Tokyo (JP)

(*) Notice: Subject to any disclaimer, the term of this patent is extended or adjusted under 35 U.S.C. 154(b) by 0 days.

(21) Appl. No.: 14/508,185

(22) Filed: Oct. 7, 2014

(65) Prior Publication Data
US 2015/0031885 A1    Jan. 29, 2015

Related U.S. Application Data (62) Division of application No. 13/877,037, filed as application No. PCT/JP2011/072329 on Sep. 29, 2011.

(30) Foreign Application Priority Data

Sep. 30, 2010 (JP) ................. 2010-221620

(51) Int. Cl.
| | | |
|---|---|---|
| C07D 241/24 | (2006.01) | |
| A61K 9/00 | (2006.01) | |
| A61K 9/19 | (2006.01) | |
| A61K 31/4965 | (2006.01) | |
| A61K 31/497 | (2006.01) | |
| A61K 47/18 | (2006.01) | |
| A61K 47/22 | (2006.01) | |
| A61K 47/26 | (2006.01) | |
| A61K 9/08 | (2006.01) | |

(52) U.S. Cl.
CPC ............ *C07D 241/24* (2013.01); *A61K 9/0019* (2013.01); *A61K 9/08* (2013.01); *A61K 9/19* (2013.01); *A61K 31/497* (2013.01); *A61K 31/4965* (2013.01); *A61K 47/18* (2013.01); *A61K 47/183* (2013.01); *A61K 47/22* (2013.01); *A61K 47/26* (2013.01)

(58) Field of Classification Search
CPC .................................................. C07D 241/24
See application file for complete search history.

(56) References Cited

U.S. PATENT DOCUMENTS

| | | | |
|---|---|---|---|
| 4,590,269 | A | 5/1986 | Prisbe et al. |
| 4,748,174 | A | 5/1988 | Veronesi |
| 6,787,544 | B2 | 9/2004 | Furuta et al. |
| 6,800,629 | B2 | 10/2004 | Egawa et al. |
| 8,168,789 | B2 | 5/2012 | Takamatsu et al. |
| RE43,748 | E | 10/2012 | Furuta et al. |
| 2002/0013316 | A1 | 1/2002 | Furuta et al. |
| 2003/0119825 | A1 | 6/2003 | Folger et al. |
| 2006/0228411 | A1 | 10/2006 | Wu et al. |
| 2010/0087447 | A1 | 4/2010 | Maekawa |
| 2012/0010221 | A1 | 1/2012 | Kakuda et al. |
| 2013/0274472 | A1 | 10/2013 | Takakura et al. |

FOREIGN PATENT DOCUMENTS

| | | |
|---|---|---|
| EP | 1 051 978 | 11/2000 |
| JP | 62 252749 | 11/1987 |
| JP | 8 291071 | 11/1996 |
| JP | 3413406 | 6/2003 |
| JP | 2005 511720 | 4/2005 |
| JP | 2008 231067 | 10/2008 |
| JP | 2008-231067 | 10/2008 |
| WO | 00 10569 | 3/2000 |

OTHER PUBLICATIONS

Searles et al. Annealing to optimize the primary drying rate, reduce freezing-induced drying rate heterogeneity, and determine T(g)' in pharmaceutical lyophilization. Journal of Pharmaceutical Sciences, 2001, 90, 872.*
Keiko Toyo Seizai no Sekkei to Hyoka, Kabushiki Kaisha Yakugyo Jihosha, pp. 69-85, (Feb. 10, 1995).
Chushazai -sono Kiso to Chozai to Tekiyo-, 1$^{st}$ edition, Nanzando Co., Ltd., pp. 19-25, (Mar. 22, 1995).
International Search Report Issued Nov. 15, 2011 in PCT/JP11/72329 Filed Sep. 29, 2011.
Extended Search Report issued Feb. 21, 2014 in European Patent Application No. 11829249.9.
Ann W. Newman, et al., "Salt and cocrystal form selection", Preclinical development handbook, ADME and Biopharmaceutical Properties, Jan. 1, 2007, XP055101443, pp. 455-481.
"A counter ion that fulfils all needs", World Pharmaceutical Frontiers, vol. 2, Sep. 1, 2011, XP055101514, (P-document), 1 page.
Swarbrick, et al. (eds. Encyclopedia of Pharmaceutical Technology 13 (Marcel Dekker, NY 1996) pp. 453-499).
U.S. Appl. No. 14/515,673, filed Oct. 16, 2014, Takakura, et al.
Search Report as received in the corresponding Taiwan Patent Application No. 100135204 dated Feb. 5, 2015.

* cited by examiner

Primary Examiner — Brian McDowell
(74) Attorney, Agent, or Firm — Oblon, McClelland, Maier & Neustadt, L.L.P.

(57) ABSTRACT

A preparation replete with a meglumine salt of 6-fluoro-3-hydroxy-2-pyrazine carboxamide has superior solubility, and is useful as a preparation for injection.

1 Claim, 3 Drawing Sheets

MEGLUMINE SALT OF 6-FLUORO-3-HYDROXY-2-PYRAZINE CARBOXAMIDE

CROSS REFERENCE TO RELATED APPLICATIONS

The present application is a divisional of U.S. application Ser. No. 13/877,037 filed May 9, 2013, pending, which is a 35 U.S.C. §371 national stage patent application of International patent application PCT/JP2011/072329, filed on Sep. 29, 2011, published as WO/2012/043696 on Apr. 5, 2012, the text of which is incorporated by reference, and claims the benefit of the filing date of Japanese application no. 2010-221620, filed on Sep. 30, 2010, the text of which is also incorporated by reference.

TECHNICAL FIELD

The present invention relates to a meglumine salt of 6-fluoro-3-hydroxy-2-pyrazinecarboxamide (hereinafter referred to as "Compound A"), an injectable preparation containing the same and a process thereof.

BACKGROUND ART

These days, worldwide pandemic has been caused by H1N1 influenza virus and occurrence of pandemic by a further virulent virus in the future is a concern.

At present, as therapeutic agents for influenza, e.g., Oseltamivir, Zanamivir, Peramivir, Laninamivir and Amantadine are used. However, these therapeutic agents have, for example, the following drawbacks. Oseltamivir cannot be administered to patients having difficulty in oral administration. It is difficult to administer Zanamivir to children and aged persons. It takes a long time to administer Peramivir. Amantadine is ineffective against Type B influenza virus and resistant viruses have emerged. Laninamivir is an inhalation drug, which is not suitable to patients with dementia and a severe disease and it is difficult to administer it to children.

A further superior therapeutic agent for influenza has been desired. Particularly, an injection that can be administered to patients having difficulty in oral administration, children and aged persons has been desired.

Meanwhile, many reports have been published on methods for improving solubility of medicinal compounds in water. For example, a method for improving the solubility in water by changing the state of a water-insoluble medicinal compound into an amorphous state is known. In general, an amorphous state of a compound exhibits more superior solubility in water than a crystalline state thereof (PATENT DOCUMENT 1).

Compound A or a salt thereof has a superior antiviral activity and is useful as a therapeutic agent for viral infection (PATENT DOCUMENT 2). However, Compound A has low solubility in water and thus an injection of Compound A or a salt thereof has not been known yet.

The present inventors prepared an aqueous solution of a sodium salt of Compound A by using sodium hydroxide generally used as a base, and then produced a lyophilized preparation in accordance with a common method, for improving the water solubility of Compound A. The sodium salt of Compound A obtained by this process was an amorphous dry powder, thus quick dissolution thereof in water was expected. However, contrary to the expectation, the obtained lyophilized preparation was a lyophilized cake having poor solubility and required a long time to dissolve. To describe more specifically, when a solvent was added to the lyophilized preparation, the lyophilized cake changed into a poorly soluble mass substance that took a long time to dissolve. The amorphous lyophilized preparation of a sodium salt of Compound A was a preparation needing a long time to dissolve, and was difficult to handle with significant loss of convenience in use.

Meanwhile, as a method for preparing a lyophilized preparation, a process having an annealing step provided therein is known. However, the effect of the annealing step on the solubility of a lyophilized preparation differs depending on substances. Therefore, studies have been made in a trial-and-error manner (NON-PATENT DOCUMENT 1).

PRIOR ARTS REFERENCES

Patent Documents

PATENT DOCUMENT 1: JP 3413406
PATENT DOCUMENT 2: International Publication No. WO 00/10569 pamphlet
NON-PATENT DOCUMENT 1: Development of medicinal drug, Vol. 11, page 393, 2000

DISCLOSURE OF THE INVENTION

Problem to be Solved by the Invention

There is a need for the development of an injectable preparation of Compound A or a salt thereof with superior solubility.

Means for Solving the Problems

The present inventors have intensively conducted studies with the view to attaining the above desire. As a result, they have found that
(1) a meglumine salt of Compound A (hereinafter referred to as "Salt A") can also be present in an amorphous or crystalline state,
(2) the solubility of Salt A in water is high,
(3) the dissolution rate of amorphous Salt A in water, the dissolution rate of a crystal of Salt A in water, and the dissolution rate of a milled crystal of Salt A in water are significantly high, and
(4) a preparation containing amorphous Salt A, a crystal of Salt A and/or a milled crystal of Salt A is superior in solubility.

More specifically, amorphous Salt A can be produced by lyophilizing an aqueous solution of Salt A. Amorphous Salt A has high solubility and significantly high dissolution rate in water. Thus, a preparation containing amorphous Salt A is superior in solubility and useful as an injectable preparation.

A crystal of Salt A can be produced by precipitating a crystal from a solution of Salt A. The crystal has high solubility and significantly high dissolution rate in water. Thus, a preparation containing a crystal of Salt A is superior in solubility and useful as an injectable preparation.

Furthermore, a milled crystal of Salt A has high solubility and significantly high dissolution rate in water. Thus, a preparation containing a milled crystal of Salt A is superior in solubility and useful as an injectable preparation.

A powder filling method is known as a technique for filling a vial, etc. with a powder. However, in a powder filling method, it is difficult to accurately control the filler content and contamination with minute foreign bodies occurs easily, when compared to a method that divides a solution into small portions. For these reasons, as a process for producing a solid injection, a process by lyophilization is the most reliable process.

As a result of intensive studies, the present inventors have found that a lyophilized preparation of a crystal of Salt A having significantly high dissolution rate can be produced in a short crystallization time by controlling the temperature (crystallization temperature) range in a temperature-increasing step after primary freezing in lyophilization. More specifically, a crystal of Salt A can be produced by providing a step of increasing temperature after the primary freezing of lyophilization. The resultant crystal has high solubility in water and significantly high dissolution rate, even though it is not milled. Therefore, the preparation containing the crystal is superior in solubility and useful as an injectable preparation.

As a result of intensive studies conducted repeatedly, the present inventors have found that a further superior lyophilized preparation can be produced by adding additives to an aqueous solution of Salt A to be subjected to lyophilization. In such a manner, the present invention has been accomplished.

Meanwhile, it is known that a crystalline state changes to an amorphous state when water is removed from the crystal of a hydrate (Yu L., Advanced Drug Delivery Reviews, Vol. 48, page 29, 2001).

However, the crystal of Salt A of the present invention does not change to an amorphous state even if a dehydration operation is applied during lyophilization. In addition, a lyophilized preparation of Salt A of the present invention has more superior solubility and much higher stability, compared to the amorphous lyophilized preparation of a sodium salt of Compound A.

A superior lyophilized preparation of a crystal of Salt A can be produced according to the process of the present invention. The lyophilized preparation can be easily maintained in aseptic conditions and from which insoluble foreign bodies can be easily removed. Therefore, the lyophilized preparation is an injection superior in usability.

More specifically, the present invention is as follows:
1. Salt A or a hydrate thereof. Salt A or a hydrate thereof has high solubility in water and significantly high dissolution rate.
2. A crystal of a Salt A or a hydrate thereof. The crystal has high solubility in water and significantly high dissolution rate.
3. Amorphous Salt A. The amorphous Salt A has high solubility in water and significantly high dissolution rate.
4. An injectable preparation containing Salt A or a hydrate thereof. The injectable preparation is superior in solubility.
5. An injectable preparation containing a crystal of Salt A or a hydrate thereof. The injectable preparation is superior in solubility.
6. An injectable preparation containing an amorphous Salt A or a hydrate thereof. The injectable preparation is superior in solubility.
7. The injectable preparation according to 4 or 5 above, further containing an amino acid and a saccharide, or an amino acid and a sugar alcohol. The injectable preparation is superior in solubility.
8. A lyophilized preparation containing Salt A. The lyophilized preparation is superior in solubility.
9. A lyophilized preparation containing a crystal of Salt A. The lyophilized preparation is superior in solubility.
10. A lyophilized preparation containing amorphous Salt A. The lyophilized preparation is superior in solubility.
11. The lyophilized preparation according to 8 or 9 above, further containing an amino acid and a saccharide, or an amino acid and a sugar alcohol. The lyophilized preparation is superior in solubility.
12. A process for producing a lyophilized preparation containing a crystal of Salt A, including the following steps: (1) cooling an aqueous solution containing Compound A and meglumine to produce a frozen product; (2) increasing the temperature of the frozen product; (3) further cooling the frozen product; and (4) carrying out lyophilization. The process can produce a lyophilized preparation of a crystal of Salt A, which has significantly high dissolution rate, in a short crystallization time.
13. The process according to 12 above, wherein the achieving temperature of the frozen product falls within the range of −20 to −5° C. in the step of increasing the temperature of the frozen product. By setting the temperature of the frozen product so as to fall within the range of −20 to −5° C., a further superior lyophilized preparation of a crystal of Salt A can be produced.

Advantages of the Invention

Salt A of the present invention is superior in solubility in water and useful as a drug substance of an injectable preparation.

Furthermore, a preparation containing Salt A of the present invention is useful as an injectable preparation which is superior in solubility and stability and even satisfactory in appearance.

Moreover, the process for producing Salt A of the present invention is useful as a process for producing a lyophilized preparation of a crystal of Salt A which is superior in solubility and stability and even satisfactory in appearance.

MODE FOR CARRYING OUT THE INVENTION

Hereinafter, the present invention will be described in detail.

Compound A can be produced by a method described, for example, in PATENT DOCUMENT 2. Compound A has a tautomer: 6-fluoro-3-oxo-3,4-dihydro-2-pyrazinecarboxamide. This tautomer is included in the present invention.

Salt A of the present invention and an injectable preparation containing Salt A can be produced, for example, according to the following processes.

Process 1: Crystal of Salt A Monohydrate

A crystal of Salt A monohydrate can be produced by adding Compound A and meglumine to water, heating the mixture to dissolve, adding 2-propanol and collecting a precipitated crystal by filtration.

The amount of water is satisfactorily 1 to 10 times (v/w), and preferably 2 to 4 times (v/w) as large as that of Compound A.

The amount of meglumine is satisfactorily 1.0 time (mole) or above, and preferably 1.0 to 1.5 times (mole) as large as that of Compound A.

The temperature of the reaction with meglumine is satisfactorily 30 to 100° C. and preferably 40 to 80° C.

The amount of 2-propanol is satisfactorily 5 to 50 times (v/w), and preferably 10 to 15 times (v/w) as large as that of Compound A.

An injectable preparation can be produced by filling a vial, etc. with the crystal of Salt A monohydrate and/or the milled crystal of Salt A monohydrate thus obtained.

Process 2: Crystal of Salt A Anhydrate

A crystal of Salt A anhydrate can be produced by allowing a crystal of Salt A monohydrate to stand still at −20 to 60° C. under reduced pressure.

The standstill time is satisfactorily 0.5 to 120 hours and preferably 1 to 72 hours.

The degree of pressure reduction is not particularly limited; however it is satisfactorily 100 Pa or below and preferably 50 Pa or below.

Alternatively, a crystal of Salt A anhydrate can be produced by allowing a crystal of Salt A monohydrate to stand still under heating.

The heating temperature is satisfactorily 30° C. or above, preferably 50° C. to 110° C. and more preferably 50° C. to 90° C.

An injectable preparation can be produced by filling a vial, etc. with the crystal of Salt A anhydrate and/or the milled crystal of Salt A anhydrate thus obtained.

Alternatively, an injectable preparation of a Salt A anhydrate can be produced by grinding the crystal of Salt A monohydrate and then drying it in the same manner as mentioned above.

Process 3: Amorphous Salt A (Lyophilization)

Amorphous Salt A can be produced by lyophilizing an aqueous solution of Compound A and meglumine.

The amount of water is satisfactorily 10 to 100 times (v/w), and preferably 10 to 50 times (v/w) as large as that of Compound A.

Meglumine is added such that the pH of the aqueous solution becomes satisfactorily 4.0 to 10 and preferably 7.0 to 9.0.

Lyophilization may be performed, for example, by freezing an aqueous solution of Compound A and meglumine at −40° C. or below and maintaining the temperature of the resultant product at a collapse temperature or below.

Process 4: Crystal of Salt A (Lyophilization)

(1) First Step (Primary Freezing Step)

An aqueous solution of Compound A and meglumine can be frozen to obtain an amorphous frozen product.

The amount of water is satisfactorily 10 to 100 times (v/w), and preferably 10 to 50 times (v/w) as large as that of Compound A.

Meglumine is added such that the pH of the aqueous solution becomes 4.0 to 10 and preferably 7.0 to 9.0.

The temperature of the primary freezing step is satisfactorily a collapse temperature or below. In the case of the present invention, the temperature of −60 to −40° C. is preferable.

The period of time for the primary freezing step is satisfactorily 1 to 10 hours and preferably 2 to 5 hours.

(2) Second Step (Annealing Step)

The temperature of the amorphous frozen product is increased and the frozen product is maintained for a preset time (annealing) to allow crystallization to proceed to obtain a crystalline frozen product.

The temperature, at which thawing of the frozen product dose not occur and crystallization proceeds to the extent that the frozen product maintains a frozen state, may be satisfactory in the annealing step; preferably −20 to −2° C., more preferably −20 to −5° C., and further preferably −15 to −5° C.

The period of time for maintaining the annealing step is satisfactorily 0.5 to 48 hours and preferably 1 to 24 hours.

(3) Third Step (Secondary Freezing Step)

Subsequently, the crystalline frozen product is cooled again.

The temperature of the secondary freezing step is preferably −60 to −30° C.

The period of time for the secondary freezing step is satisfactorily 1 to 10 hours and preferably 2 to 5 hours.

(4) Fourth Step (Lyophilization Step)

Subsequently, pressure reduction treatment can be performed to produce a lyophilized preparation.

This step can be performed in accordance with a lyophilization method usually used, for example, in two steps, i.e., a primary drying step and a secondary drying step.

The primary drying step is carried out under reduced pressure while product temperature is maintained at the eutectic point or below; however, since the temperature drops as the moisture sublimates from the frozen product, the preset temperature of an apparatus may be the eutectic point or above.

The product temperature of the frozen product is satisfactorily −40 to −3° C. and preferably −30 to −5° C.

The preset temperature of an apparatus is satisfactorily −20 to 60° C. and preferably −10 to 50° C.

The degree of pressure reduction in the primary drying step is not particularly limited; however it is satisfactorily 100 Pa or below and preferably 50 Pa or below.

As the amount of sublimating moisture decreases, the rate of temperature decrease becomes slower. As a result, the product temperature increases and becomes almost equal to the preset temperature. Usually, at this time point, the primary drying step is determined to have completed.

Subsequently, the secondary drying step is carried out.

The secondary drying step is carried out at room temperature or above and preferably 30 to 60° C.

In the secondary drying step, the degree of pressure reduction is preferably enhanced in order to accelerate removal of water. The degree of pressure reduction is satisfactorily 0.5 to 10 Pa and preferably 1 to 5 Pa.

The secondary drying step may be satisfactorily carried out up until the point where the product temperature becomes almost equal to the preset temperature and a product temperature virtually does not change.

The powder X-ray diffraction pattern of a crystal of Salt A produced by the process was the same as the powder X-ray diffraction pattern of a crystal of Salt A anhydrate produced in process 2. More specifically, a lyophilized preparation of a crystal of Salt A anhydrate can be produced by the use of the process.

In the process for producing the lyophilized preparation of the present invention, a sterilization treatment or the like may be carried out in accordance with the procedure usually employed.

In the process of the present invention, since no organic solvents are used, the lyophilized preparation has no residual solvent.

The lyophilized preparation of the present invention is not harmful to a human body.

Unless otherwise, powder X-ray diffraction measurement conditions are as follows.

Powder X-ray diffraction measurement conditions:
X-rays to be used: CuKα
Applied voltage: 40 kV
Supplied current: 40 mA
Scanning axis: 2θ
Scanning range: 2θ=2 to 40°

The characteristic peaks of powder X-ray diffraction sometimes varies depending on measurement conditions. Generally, 2θ has a margin of error of ±0.2°. Accordingly, "the diffraction angle of X° represented by 2θ" refers to "a diffraction angle of ((X−0.2) to (X+0.2))° represented by 2θ".

The Salt A of the present invention includes a crystal of a monohydrate, a crystal of an anhydrate and amorphous anhydrate. Furthermore, various shapes of crystals are included in the crystal.

Additives can be added to the lyophilized preparation containing Salt A of the present invention for improving solubility and/or appearance.

The temperature range of the annealing step can be extended by adding additives.

Examples of the additives include amino acids, saccharides, sugar alcohols, salts, urea, ethyl urea, creatinine, nicotinic acid amide and trometamol. These may be used alone or as a mixture of two or more types. Examples of preferable additives include amino acids, saccharides, sugar alcohols, salts, urea, creatinine, nicotinic acid amide and trometamol.

Examples of the amino acids include glycine, L-alanine, L-phenylalanine, L-leucine, L-isoleucine, taurine, DL-methionine, L-threonine, L-glutamine, sodium L-glutamate, acetyltryptophan and L-histidine. Glycine, L-alanine, taurine and L-histidine are more preferable and glycine and L-alanine are further preferable.

Examples of the saccharides include trehalose, maltose, glucose, lactose, purified white sugar, fructose, dextran and cyclodextrin. Trehalose, maltose, glucose, lactose and purified white sugar are more preferable and trehalose and purified white sugar are further preferable.

Examples of the sugar alcohols include D-sorbitol, xylitol, inositol and D-mannitol.

Examples of the salts include sodium acetate, sodium lactate, sodium L-tartrate, sodium citrate, sodium salicylate, sodium benzoate and sodium caprylate. Sodium acetate, sodium lactate and sodium benzoate are more preferable.

Furthermore, a combination use of an amino acid and a saccharide, or an amino acid and a sugar alcohol is preferable and a combination use of an amino acid and a saccharide is more preferable.

Preferable examples of the amino acids include glycine and L-alanine.

Preferable examples of the saccharide include trehalose and purified white sugar.

Preferable examples of the sugar alcohol include D-sorbitol, xylitol and D-mannitol.

Furthermore, if necessary, conventional additives, such as an osmo-regulator, a pH regulator, a buffer, a solubilizer, a stabilizer, a surfactant, a soothing agent, and/or a preservative, may be added to the preparation of the present invention.

Examples of the osmo-regulator include sodium chloride, glycerin and propylene glycol.

Examples of the pH regulator and/or the buffer include acids such as hydrochloric acid, phosphoric acid, sulfuric acid, methanesulfonic acid, acetic acid, lactic acid, maleic acid, citric acid, tartaric acid, ascorbic acid and benzoic acid; salts such as sodium bicarbonate, sodium carbonate, sodium dihydrogenphosphate, potassium dihydrogenphosphate, disodium hydrogenphosphate, dipotassium hydrogenphosphate, trisodium phosphate, disodium citrate and sodium sulfite; and bases such as sodium hydroxide, trometamol, monoethanolamine, diethanolamine, triethanolamine, L-arginine and L-lysine.

Examples of the solubilizer include Macrogol and purified soybean lecithin.

Examples of the stabilizer include sodium hydrogen sulfite, sodium pyrosulfite, potassium pyrosulfite, sodium pyrophosphate, sodium thiosulfate, sodium metasulfobenzoate, sodium formaldehyde sulfoxylate, ethylene diamine, edetate sodium, thioglycolic acid, sodium gluconate, potassium L-glutamate, L-lysine-L-glutamate, sodium chondroitin sulfate, albumin, L-aspartic acid, L-cysteine and dibutylhydroxytoluene.

Examples of the surfactant include, sorbitan fatty acid ester, polyoxyethylene hydrogenated castor oil, polyoxyethylene sorbitan monolaurate, polyoxyethylene polyoxypropylene glycol and polysorbate.

Examples of the soothing agent include lidocaine, procaine, meprylcaine and benzyl alcohol.

Examples of the preservative include cresol, phenol, methyl paraoxybenzoate, ethyl paraoxybenzoate, benzalkonium chloride and benzethonium chloride.

In an injectable preparation of the present invention, the dose of an active ingredient is appropriately determined in accordance with dosage form, age and gender of a patient, conditions of a disease and other conditions; however, usually 0.1 to 100 mg/kg per adult per day may be administered.

In an injectable preparation of the present invention, the content of Compound A is 10 to 6000 mg and preferably 100 to 2000 mg.

In an injectable preparation of the present invention, the content of the additives to be added for improving solubility and/or appearance is 0.1 to 115% (w/w) and preferably 5 to 65% (w/w) relative to the content of Compound A.

EXAMPLES

Hereinafter, the present invention will be described by showing Examples and Experimental Examples; however, the present invention is not limited to these examples.

DMSO-$d_6$ refers to heavy dimethylsulfoxide.

The water content was measured by the Karl Fischer method.

Example 1

A suspension of Compound A (10.0 g) and meglumine (15.0 g) in water (30 mL) was heated to 50° C. for dissolution. After 2-propanol (120 mL) was added dropwise at 40° C., the mixture was cooled to 5° C. and stirred at the same temperature for one hour. A solid substance was collected by filtration to obtain a light-yellow crystal of Salt A monohydrate (21.3 g).

Water content: 5.2%

$^1$H-NMR (400 MHz, DMSO-$d_6$) δ (ppm): 10.43 (1H, brs), 7.93 (1H, d, J=9.0 Hz), 7.27 (1H, brs), 3.90-3.80 (1H, m), 3.70-3.55 (2H, m), 3.55-3.35 (3H, m), 3.05-2.85 (2H, m), 2.54 (3H, s)

Figure 1:
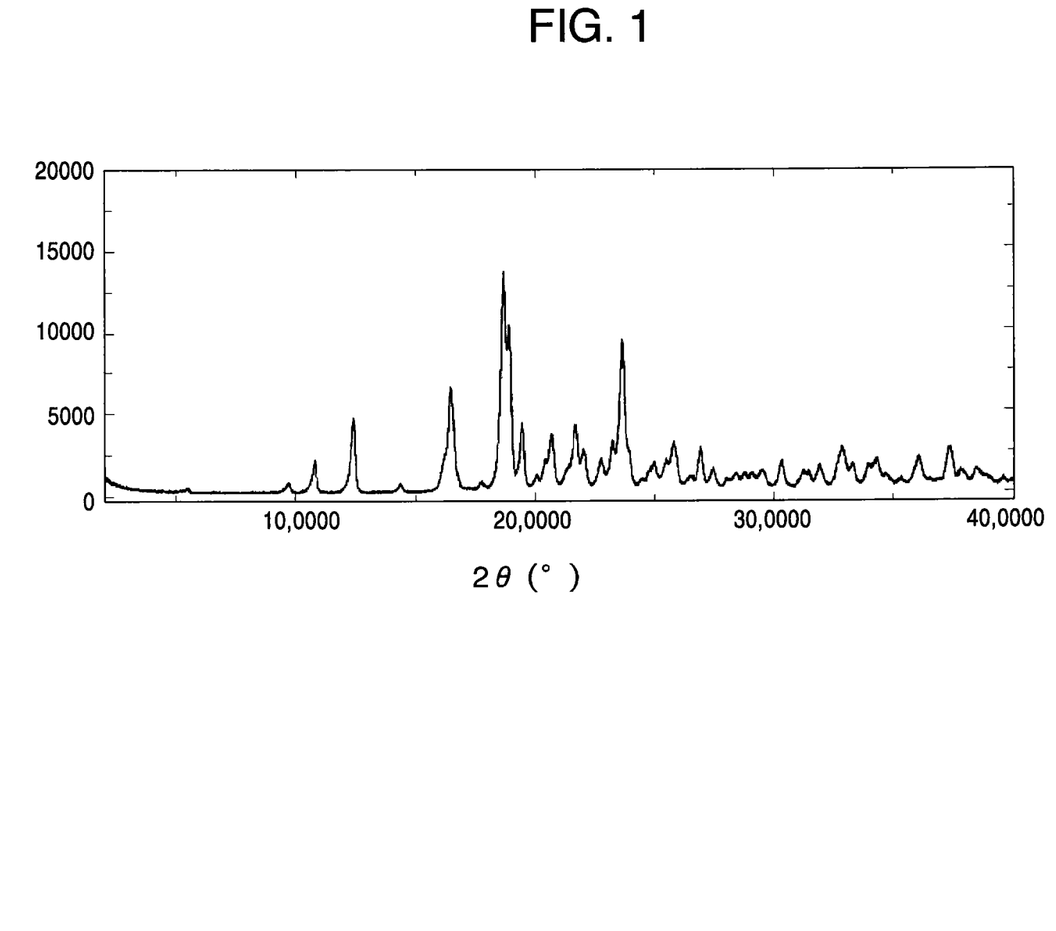
FIG. 1 is a powder X-ray diffraction pattern of a crystal of a meglumine salt (monohydrate) of 6-fluoro-3-hydroxy-2-pyrazinecarboxamide.

The result of powder X-ray diffraction of the crystal of Salt A monohydrate is shown in FIG. 1 and Table 1.

TABLE 1

| 2θ | d | Relative intensity |
|---|---|---|
| 10.8 | 8.20 | 15 |
| 12.4 | 7.13 | 35 |
| 16.2 | 5.46 | 15 |
| 16.5 | 5.38 | 49 |
| 18.7 | 4.75 | 100 |
| 18.9 | 4.69 | 75 |
| 19.5 | 4.56 | 30 |
| 20.7 | 4.29 | 24 |
| 21.7 | 4.10 | 27 |
| 22.0 | 4.03 | 16 |
| 23.2 | 3.83 | 18 |
| 23.6 | 3.76 | 67 |

Example 2

The crystal obtained in Example 1 was milled and passed through No. 60 (250 μm) sieve to obtain a powder remaining on No. 282 (53 μm) sieve. Each vial was filled with the powder (1.41 g) to obtain an injectable preparation of a monohydrate crystal.

Example 3-1

The crystal (1.35 g) obtained in Example 1 was allowed to stand still at 40° C. under vacuum (50 Pa or below) for 64 hours to obtain a crystal of an anhydrate.
Water content: 0.07%
In the powder X-ray diffraction pattern of the obtained crystal, peaks were observed at 2θ (°): 11.3, 13.0, 17.0, 19.7, 20.5, 22.0, 24.2, 26.4, 28.1.

Example 3-2

Figure 3:
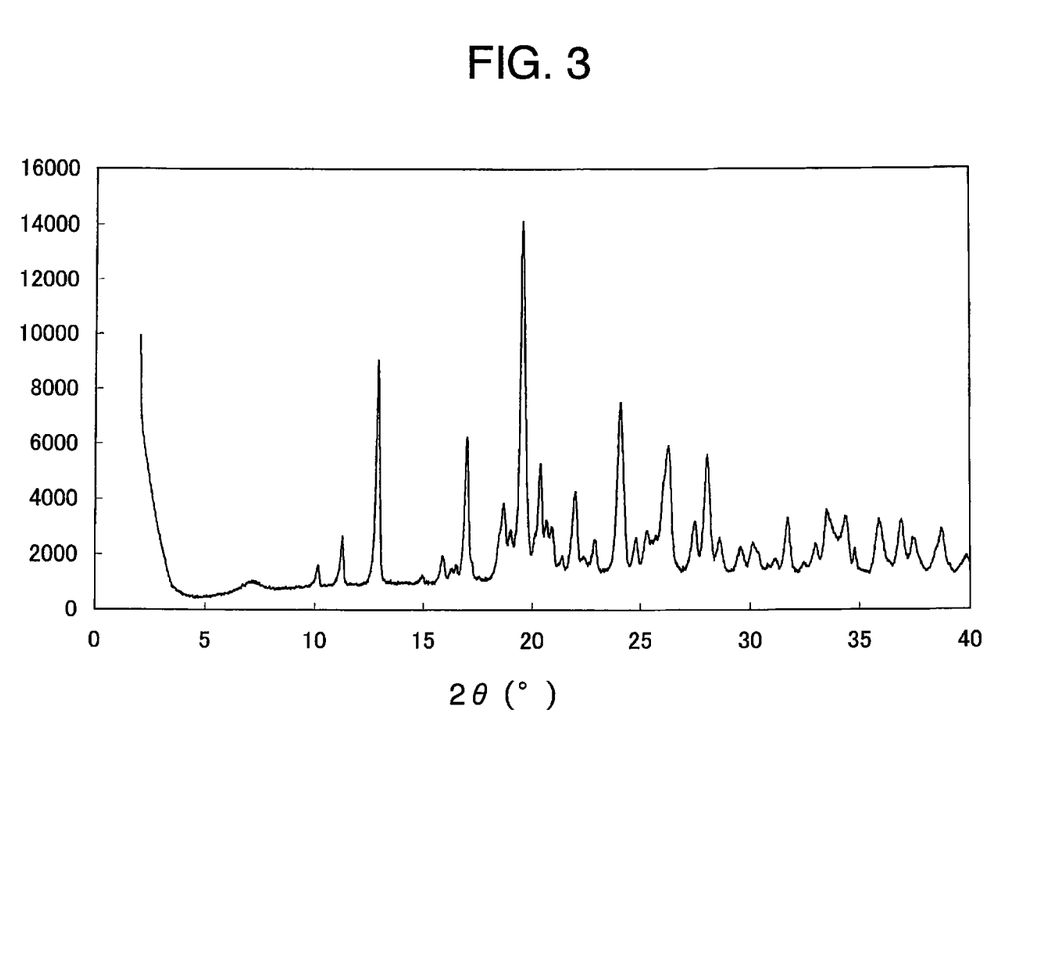
FIG. 3 is a powder X-ray diffraction pattern of a crystal of an anhydrous meglumine salt of 6-fluoro-3-hydroxy-2-pyrazinecarboxamide.

The crystal (86 mg) obtained in Example 1 was allowed to stand still at 80 to 90° C. for 5 minutes and thereafter at 90° C. for 180 minutes to obtain a crystal of an anhydrate.
The result of powder X-ray diffraction of the crystal of the anhydrate is shown in FIG. 3 and Table 2.
The powder X-ray diffraction pattern coincided with that of Example 3-1.
Powder X-ray diffraction measurement conditions:
X-rays to be used: CuKα1, CuKα2, CuKβ
Applied voltage: 45 kV
Supplied current: 40 mA
Scanning axis: 2θ
Scanning range: 2θ=2 to 40°
Measurement temperature: 90° C.

TABLE 2

| 2θ | Relative intensity |
|---|---|
| 10.2 | 12 |
| 11.3 | 19 |
| 13.0 | 64 |
| 15.9 | 14 |
| 17.0 | 44 |
| 18.7 | 27 |
| 19.7 | 100 |
| 20.5 | 37 |
| 22.0 | 30 |
| 24.2 | 53 |
| 26.4 | 42 |
| 28.1 | 40 |

Example 4

The injectable preparation obtained in Example 2 was allowed to stand still at 40° C. under vacuum (50 Pa or below) for 60 hours to obtain an injectable preparation of a crystal of the anhydrate.
Water content: 0.17%

Example 5

Figure 2:
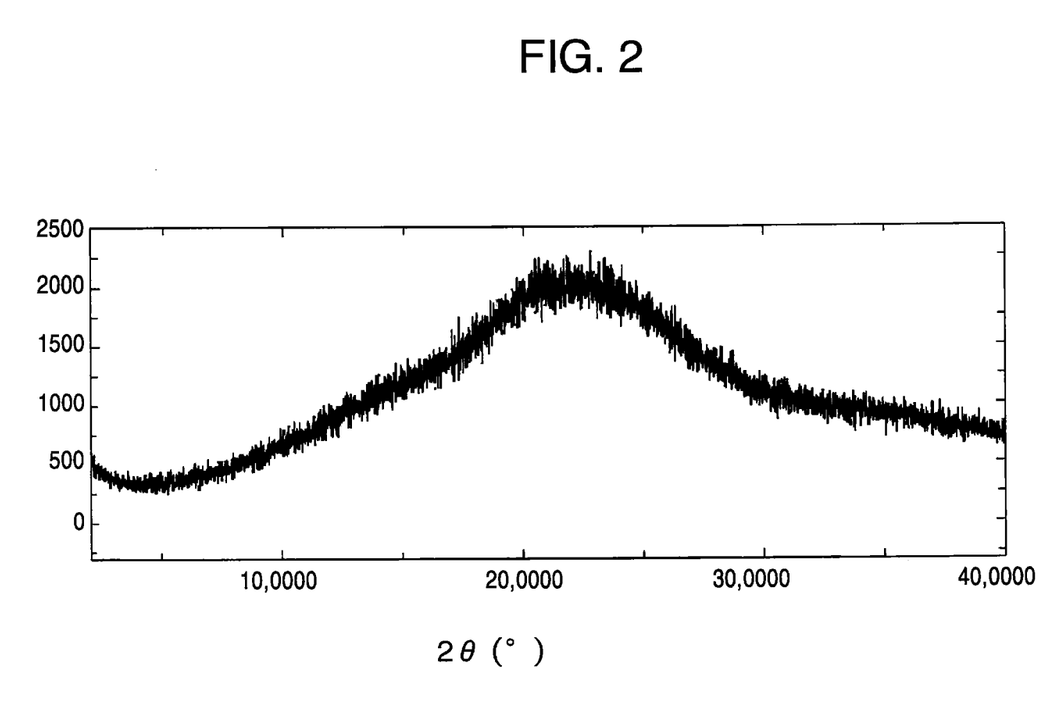
FIG. 2 is a powder X-ray diffraction pattern of an amorphous meglumine salt of 6-fluoro-3-hydroxy-2-pyrazinecarboxamide.

To a suspension of Compound A (45.1 g) in Water for Injection (500 mL) was added meglumine (55.9 g), and the mixture was stirred to dissolve Compound A. After to the solution was added Water for Injection to give a total volume of 600 mL, the mixture was filtered through a 0.22-μm membrane filter to obtain a liquid preparation (pH 7.6). Each vial was filled with the liquid preparation (8 mL), lyophilized and then closed airtight to obtain a lyophilized preparation of an amorphous product.
Water content: 0.17%
The result of powder X-ray diffraction of the lyophilized preparation is shown in FIG. 2.
Lyophilization Method
1. Vials were cooled at the shelf temperature of −60° C. to freeze the content.
2. The temperature of the vials was increased to the shelf temperature of −20° C. under vacuum (50 Pa or below) and the vials were maintained at the same pressure and the same temperature for 64 hours.
3. The temperature of the vials was increased to the shelf temperature of −10° C. and the vials were maintained at the same pressure and the same temperature for 7 hours.
4. The temperature of the vials was increased to the shelf temperature of 0° C. and the vials were maintained at the same pressure and the same temperature for 11 hours.
5. The temperature of the vials was increased to the shelf temperature of 20° C. and the vials were maintained at the same pressure and the same temperature for 10 hours.
6. The temperature of the vials was increased to the shelf temperature of 40° C. and the vials were maintained at the same pressure and the same temperature for 17 hours.

Example 6

To a suspension of Compound A (72.0 g) in Water for Injection (1000 mL) was added meglumine (90.7 g), and the mixture was stirred to dissolve Compound A. To the obtained solution was added Water for Injection to give a total volume of 1200 mL. Thereafter, the mixture was filtered through a 0.22-μm membrane filter to obtain a liquid preparation (pH 8.0). Each vial was filled with the liquid preparation (10 mL), lyophilized and then closed airtight to obtain a lyophilized preparation of a crystal.
Water content: 0.01%
In the powder X-ray diffraction pattern of the lyophilized preparation, the same peaks as those of the crystal of Salt A anhydrate observed in Example 3 were observed.
Lyophilization Method
1. Vials were cooled at the shelf temperature of −60° C. to freeze the content.
2. The temperature of the vials was increased to the shelf temperature of −5° C. and the vials were maintained at the same temperature for 25 hours.
3. The temperature of the vials was cooled to the shelf temperature of −55° C. or below and the vials were maintained at the same temperature for 3 hours.
4. The temperature of the vials was increased to the shelf temperature of 40° C. under vacuum (50 Pa or below) and the vials were maintained at the same pressure and the same temperature for 60 hours.

Example 7

To a suspension of Compound A (132 g) in Water for Injection (1900 mL) was added meglumine (166 g), and the mixture was stirred to dissolve Compound A. To the obtained solution was added Water for Injection to give a total volume of 2200 mL. Thereafter, the mixture was filtered through a 0.22-μm membrane filter to obtain a liquid preparation (pH 8.0). Each vial was filled with the liquid preparation (10 mL), lyophilized and then closed airtight to obtain a lyophilized preparation of a crystal.
Water content: 0.01%
In the powder X-ray diffraction pattern of the lyophilized preparation, the same peaks as those of the crystal of Salt A anhydrate observed in Example 3 were observed.

Lyophilization Method
1. Vials were cooled at the shelf temperature of −60° C. to freeze the content.
2. The temperature of the vials was increased to the shelf temperature of −10° C. and the vials were maintained at the same temperature for 24 hours.
3. The temperature of the vials was cooled to the shelf temperature of −55° C. or below and the vials were maintained at the same temperature for 2 hours.
4. The temperature of the vials was increased to the shelf temperature of 40° C. under vacuum (50 Pa or below) and the vials were maintained at the same pressure and the same temperature for 48 hours.

Example 8

To a suspension of Compound A (132 g) in Water for Injection (1800 mL) was added meglumine (166 g), and the mixture was stirred to dissolve Compound A. To the obtained solution was added Water for Injection to give a total volume of 2200 mL. Thereafter, the mixture was filtered through a 0.22-μm membrane filter to obtain a liquid preparation (pH 8.0). Each vial was filled with the liquid preparation (10 mL), lyophilized and then closed airtight to obtain a lyophilized preparation of a crystal.
Water content: 0.00%
In the powder X-ray diffraction pattern of the lyophilized preparation, the same peaks as those of the crystal of Salt A anhydrate observed in Example 3 were observed.
Lyophilization Method
1. Vials were cooled at the shelf temperature of −60° C. to freeze the content.
2. The temperature of the vials was increased to the shelf temperature of −15° C. and the vials were maintained at the same temperature for 24 hours.
3. The temperature of the vials was cooled to the shelf temperature of −55° C. or below and the vials were maintained at the same temperature for 2 hours.
4. The temperature of the vials was increased to the shelf temperature of 40° C. under vacuum (50 Pa or below) and the vials were maintained at the same pressure and the same temperature for 46 hours.

Example 9

To a suspension of Compound A (54.0 g) in Water for Injection (750 mL) was added meglumine (68.0 g), and the mixture was stirred to dissolve Compound A. To the obtained solution was added Water for Injection to give a total volume of 900 mL. Thereafter, the mixture was filtered through a 0.22-μm membrane filter to obtain a liquid preparation (pH 8.0). Each vial was filled with the liquid preparation (10 mL), lyophilized and then closed airtight to obtain a lyophilized preparation of a crystal
Water content: 0.02%
In the powder X-ray diffraction pattern of the lyophilized preparation, the same peaks as those of the crystal of Salt A anhydrate observed in Example 3 were observed.
Lyophilization Method
1. Vials were cooled at the shelf temperature of −60° C. to freeze the content.
2. The temperature of the vials was increased to the shelf temperature of −30° C. and the vials were maintained at the same temperature for 14 hours.
3. The temperature of the vials was increased to the shelf temperature of −25° C. and the vials were maintained at the same temperature for 25 hours.
4. The temperature of the vials was increased to the shelf temperature of −20° C. and the vials were maintained at the same temperature for 25 hours.
5. The temperature of the vials was cooled to the shelf temperature of −55° C. or below and the vials were maintained at the same temperature for 2 hours.
6. The temperature of the vials was increased to the shelf temperature of 40° C. under vacuum (50 Pa or below) and the vials were maintained at the same pressure and the same temperature for 50 hours.

Example 10

To a suspension of Compound A (73.2 g) in Water for Injection (1000 mL) was added meglumine (91.9 g), and the mixture was stirred to dissolve Compound A. To the obtained solution was added Water for Injection to give a total volume of 1220 mL. To this solution (200 mL) was added glycine (2.00 g), and it was dissolved, then filtered through a 0.22-μm membrane filter to obtain a liquid preparation (pH 7.8). Each vial was filled with the liquid preparation (10 mL), lyophilized and then closed airtight to obtain a lyophilized preparation of a crystal.
Water content: 0.03%
In the powder X-ray diffraction pattern of the lyophilized preparation, the same peaks as those of the crystal of Salt A anhydrate observed in Example 3 were observed.
Lyophilization method: the same as in Example 7.

Example 11

To a suspension of Compound A (73.2 g) in Water for Injection (1000 mL) was added meglumine (91.9 g), and the mixture was stirred to dissolve Compound A. To the obtained solution was added Water for Injection to give a total volume of 1220 mL. To the solution (200 mL) was added L-alanine (2.00 g), and it was dissolved. Thereafter, the mixture was filtered through a 0.22-μm membrane filter to obtain a liquid preparation (pH 7.9). Each vial was filled with the liquid preparation (10 mL), lyophilized and then closed airtight to obtain a lyophilized preparation of a crystal.
Water content: 0.03%
In the powder X-ray diffraction pattern of the lyophilized preparation, the same peaks as those of the crystal of Salt A anhydrate observed in Example 3 were observed.
Lyophilization method: the same as in Example 7.

Example 12

To the liquid preparation (35 mL) produced in the same manner as in Example 7 was added L-histidine (0.35 g), and a solution (pH 8.0) was obtained. Each vial was filled with the solution (10 mL), lyophilized and then closed airtight to obtain a lyophilized preparation of a crystal.
Lyophilization method: the same as in Example 7.

Example 13

To a suspension of Compound A (69.0 g) in Water for Injection (760 mL) was added meglumine (85.8 g), and the mixture was stirred to dissolve Compound A. To the obtained solution was added Water for Injection to give a total volume of 920 mL. To the solution (240 mL) was added taurine (1.20 g), and it was dissolved. Thereafter, the mixture was filtered through a 0.22-μm membrane filter to obtain a liquid preparation (pH 7.6). Each vial was filled with the liquid preparation (8 mL), lyophilized and then closed airtight to obtain a lyophilized preparation of a crystal.
Water content: 0.02%
Lyophilization method: the same as in Example 7.

Example 14

To the liquid preparation (100 mL) produced in the same manner as in Example 7 was added trehalose (1.00 g), and a solution (pH 8.0) was obtained. Each vial was filled with the solution (10 mL), lyophilized and then closed airtight to obtain a lyophilized preparation of a crystal.
Water content: 0.05%
Lyophilization method: the same as in Example 7.
In the powder X-ray diffraction pattern of the lyophilized preparation, the same peaks as those of the crystal of Salt A anhydrate observed in Example 3 were observed.

Example 15

To the liquid preparation (160 mL) produced in the same manner as in Example 7 was added trehalose (3.20 g), and a solution (pH 8.0) was obtained. Each vial was filled with the solution (10 mL), lyophilized and then closed airtight to obtain a lyophilized preparation of a crystal.
Lyophilization method: the same as in Example 7.

Example 16

To the liquid preparation (55 mL) produced in the same manner as in Example 7 was added D-maltose monohydrate (1.65 g), and a solution (pH 8.1) was obtained. Each vial was filled with the solution (10 mL), lyophilized and then closed airtight to obtain a lyophilized preparation of a crystal.
Lyophilization method: the same as in Example 7.

Example 17

To a suspension of Compound A (73.2 g) in Water for Injection (1000 mL) was added meglumine (91.9 g), and the mixture was stirred to dissolve Compound A. To the obtained solution was added Water for Injection to give a total volume of 1220 mL. To the solution (200 mL) was added glucose (2.00 g), and it was dissolved. Thereafter, the mixture was filtered through a 0.22-μm membrane filter to obtain a liquid preparation (pH 8.0). Each vial was filled with the liquid preparation (10 mL), lyophilized and then closed airtight to obtain a lyophilized preparation of a crystal.
Water content: 0.04%
Lyophilization method: the same as in Example 7.

Example 18

To the liquid preparation (55 mL) produced in the same manner as in Example 7 was added lactose (1.65 g), and a solution (pH 8.0) was obtained. Each vial was filled with the solution (10 mL), lyophilized and then closed airtight to obtain a lyophilized preparation of a crystal.
Lyophilization method: the same as in Example 7.

Example 19

Each vial was filled with the liquid preparation (pH 8.1, 10 mL) produced in the same manner as in Example 7, and purified white sugar (0.30 g)(manufactured by Ensuiko Sugar Refining Co., Ltd.) was added and dissolved. After lyophilization, the vials were closed airtight to obtain a lyophilized preparation of a crystal.
Lyophilization method: the same as in Example 7.

Example 20

To the liquid preparation (160 mL) produced in the same manner as in Example 7 was added D-sorbitol (1.60 g), and a solution (pH 8.0) was obtained. Each vial was filled with the solution (10 mL), lyophilized and then closed airtight to obtain a lyophilized preparation of a crystal.
Lyophilization method: the same as in Example 7.

Example 21

To the liquid preparation (35 mL) produced in the same manner as in Example 7 was added xylitol (0.35 g), and a solution (pH 8.0) was obtained. Each vial was filled with the solution (10 mL), lyophilized and then closed airtight to obtain a lyophilized preparation of a crystal.
Lyophilization method: the same as in Example 7.

Example 22

To a suspension of Compound A (69.0 g) in Water for Injection (760 mL) was added meglumine (85.8 g), and the mixture was stirred to dissolve Compound A. To the obtained solution was added Water for Injection to give a total volume of 920 mL. Thereafter, the mixture was filtered through a 0.22-μm membrane filter to obtain a liquid preparation (pH 7.6). Each vial was filled with the liquid preparation (8 mL) and inositol (0.10 g) was added and dissolved. After lyophilization, the vials were closed airtight to obtain a lyophilized preparation of a crystal.
Lyophilization method: the same as in Example 7.

Example 23

To the liquid preparation (160 mL) produced in the same manner as in Example 7 was added D-mannitol (1.60 g), and a solution (pH 8.1) was obtained. Each vial was filled with the solution (10 mL), lyophilized and then closed airtight to obtain a lyophilized preparation of a crystal.
Lyophilization method: the same as in Example 7.

Example 24

To the liquid preparation (55 mL) produced in the same manner as in Example 7 was added sodium acetate trihydrate (0.55 g), and a solution (pH 8.1) was obtained. Each vial was filled with the solution (10 mL), lyophilized and then closed airtight to obtain a lyophilized preparation of a crystal.
Lyophilization method: the same as in Example 7.

Example 25

To the liquid preparation (55 mL) produced in the same manner as in Example 7 was added sodium lactate (50% solution, 1.11 g), and a solution (pH 8.1) was obtained. Each vial was filled with the solution (10 mL), lyophilized and then closed airtight to obtain a lyophilized preparation of a crystal.
Lyophilization method: the same as in Example 7.

Example 26

To the liquid preparation (55 mL) produced in the same manner as in Example 7 was added sodium benzoate (0.55 g), and a solution (pH 8.1) was obtained. Each vial was filled with the solution (10 mL), lyophilized and then closed airtight to obtain a lyophilized preparation of a crystal.
Lyophilization method: the same as in Example 7.

Example 27

To the liquid preparation (35 mL) produced in the same manner as in Example 7 was added creatinine (0.35 g), and a solution (pH 8.0) was obtained. Each vial was filled with the solution (10 mL), lyophilized and then closed airtight to obtain a lyophilized preparation of a crystal.
Lyophilization method: the same as in Example 7.

Example 28

To a suspension of Compound A (69.0 g) in Water for Injection (760 mL) was added meglumine (85.8 g), and the mixture was stirred to dissolve Compound A. To the obtained solution was added Water for Injection to give a total volume of 920 mL. To the solution (240 mL) was added urea (1.50 g), and it was dissolved, then filtered through a 0.22-μm membrane filter to obtain a liquid preparation (pH 7.7). Each vial was filled with the liquid preparation (8 mL), lyophilized and then closed airtight to obtain a lyophilized preparation of a crystal.
Water content: 0.02%
Lyophilization method: the same as in Example 7.

Example 29

To a suspension of Compound A (15.0 g) in Water for Injection (160 mL) were added meglumine (18.6 g) and nicotinic acid amide (1.25 g), and the mixture was stirred to dissolve Compound A. To the obtained solution was added Water for Injection to give a total volume of 200 mL. Thereafter the mixture was filtered through a 0.22-μm membrane filter to obtain a liquid preparation (pH 7.8). Each vial was filled with the liquid preparation (8 mL), lyophilized and then closed airtight to obtain a lyophilized preparation of a crystal.
Water content: 0.02%
Lyophilization Method
1. Vials were cooled at the shelf temperature of −60° C. to freeze the content.
2. The temperature of the vials was increased to the shelf temperature of −10° C. and the vials were maintained at the same temperature for 24 hours.
3. The temperature of the vials was cooled to the shelf temperature of −55° C. or below and the vials were maintained at the same temperature for 2 hours.
4. The temperature of the vials was increased to the shelf temperature of 10° C. under vacuum (50 Pa or below) and the vials were maintained at the same pressure and the same temperature for 30 hours.
5. The temperature of the vials was increased to the shelf temperature of 20° C. and the vials were maintained at the same pressure and the same temperature for 2 hours.
6. The temperature of the vials was increased to the shelf temperature of 40° C. and the vials were maintained at the same pressure and the same temperature for 10 hours.

Example 30

To the liquid preparation (55 mL) produced in the same manner as in Example 7 was added trometamol (0.55 g), and a solution (pH 8.9) was obtained. Each vial was filled with the solution (10 mL), lyophilized and then closed airtight to obtain a lyophilized preparation of a crystal.
Lyophilization method: the same as in Example 7.

Example 31

To the liquid preparation (210 mL) produced in the same manner as in Example 7 were added glycine (2.10 g) and trehalose (2.10 g), and a solution (pH 7.9) was obtained. Each vial was filled with the solution (10 mL), lyophilized and then closed airtight to obtain a lyophilized preparation of a crystal.
Lyophilization method: the same as in Example 7.

Example 32

To the liquid preparation (210 mL) produced in the same manner as in Example 7 were added L-alanine (2.10 g) and trehalose (2.10 g), and a solution (pH 8.0) was obtained. Each vial was filled with the solution (10 mL), lyophilized and then closed airtight to obtain a lyophilized preparation of a crystal.
Lyophilization method: the same as in Example 7.
Water content: 0.05%
In the powder X-ray diffraction pattern of the lyophilized preparation, the same peaks as those of the crystal of Salt A anhydrate observed in Example 3 were observed.

Example 33

Vials were filled with the liquid preparation (pH 8.1, 10 mL) produced in the same manner as in Example 7 and glycine (0.10 g) and purified white sugar (0.10 g, manufactured by Ensuiko Sugar Refining Co., Ltd.) were added and dissolved. After lyophilization, the vials were closed airtight to obtain a lyophilized preparation of a crystal.
Lyophilization method: the same as in Example 7.

Example 34

Vials were filled with the liquid preparation (pH 8.1, 10 mL) produced in the same manner as in Example 7 and L-alanine (0.10 g) and purified white sugar (0.10 g, manufactured by Ensuiko Sugar Refining Co., Ltd.) were added and dissolved. After lyophilization, the vials were closed airtight to obtain a lyophilized preparation of a crystal.
Lyophilization method: the same as in Example 7.

Example 35

To the liquid preparation (90 mL) produced in the same manner as in Example 7 were added glycine (0.90 g) and D-sorbitol (0.90 g), and a solution (pH 8.0) was obtained. Each vial was filled with the solution (10 mL), lyophilized and then closed airtight to obtain a lyophilized preparation of a crystal.
Lyophilization method: the same as in Example 7.

Example 36

To the liquid preparation (210 mL) produced in the same manner as in Example 7 were added L-alanine (2.10 g) and D-sorbitol (2.10 g), and a solution (pH 8.0) was obtained. Each vial was filled with the solution (10 mL), lyophilized and then closed airtight to obtain a lyophilized preparation of a crystal.
Lyophilization method: the same as in Example 7.

Example 37

To the liquid preparation (90 mL) produced in the same manner as in Example 7 were added glycine (0.90 g) and xylitol (0.90 g), and a solution (pH 7.9) was obtained. Each vial was filled with the solution (10 mL), lyophilized and then closed airtight to obtain a lyophilized preparation of a crystal.
Lyophilization method: the same as in Example 7.

Example 38

To the liquid preparation (90 mL) produced in the same manner as in Example 7 were added L-alanine (0.90 g) and xylitol (0.90 g), and a solution (pH 8.0) was obtained. Each vial was filled with the solution (10 mL), lyophilized and then closed airtight to obtain a lyophilized preparation of a crystal.
Lyophilization method: the same as in Example 7.

Example 39

To the liquid preparation (90 mL) produced in the same manner as in Example 7 were added glycine (0.90 g) and D-mannitol (0.90 g), and a solution (pH 7.9) was obtained. Each vial was filled with the solution (10 mL), lyophilized and then closed airtight to obtain a lyophilized preparation of a crystal.
Lyophilization method: the same as in Example 7.

Example 40

To the liquid preparation (210 mL) produced in the same manner as in Example 7 were added L-alanine (2.10 g) and D-mannitol (2.10 g), and a solution (pH 8.0) was obtained. Each vial was filled with the solution (10 mL), lyophilized and then closed airtight to obtain a lyophilized preparation of a crystal.
Lyophilization method: the same as in Example 7.

Example 41

To a suspension of Compound A (12.0 g) in Water for Injection (180 mL) was added meglumine (14.9 g), and the mixture was stirred to dissolve Compound A. To the obtained solution was added Water for Injection to give a total volume of 200 mL. Thereafter, the mixture was filtered through a 0.22-μm membrane filter to obtain a liquid preparation (pH 7.4). Each vial was filled with the liquid preparation (10 mL), lyophilized and then closed airtight to obtain a lyophilized preparation of a crystal.
Water content: 0.03%
Lyophilization method: the same as in Example 6.

Example 42

To a suspension of Compound A (12.0 g) in Water for Injection (170 mL) was added meglumine (15.7 g), and the mixture was stirred to dissolve Compound A. To the obtained solution was added Water for Injection to give total volume of 200 mL. Thereafter, the mixture was filtered through a 0.22-μm membrane filter to obtain a liquid preparation (pH 8.5). Each vial was filled with the liquid preparation (10 mL), lyophilized and then closed airtight to obtain a lyophilized preparation of a crystal.
Water content: 0.02%
Lyophilization method: the same as in Example 6.

Example 43

Production was performed in the same manner as in Example 41 to obtain a liquid preparation (pH 7.6). Each vial was filled with the liquid preparation (10 mL), lyophilized and then closed airtight to obtain a lyophilized preparation of a crystal.
Water content: 0.01%
Lyophilization method: the same as in Example 7.

Example 44

Production was performed in the same manner as in Example 42 to obtain a liquid preparation (pH 8.5). Each vial was filled with the liquid preparation (10 mL), lyophilized and then closed airtight to obtain a lyophilized preparation of a crystal.
Water content: 0.00%
Lyophilization method: the same as in Example 7.

Example 45

To the liquid preparation (55 mL) produced in the same manner as in Example 7 were added trehalose (1.10 g) and glycine (1.10 g), and a solution (pH 7.7) was obtained. Each vial was filled with the solution (10 mL), lyophilized and then closed airtight to obtain a lyophilized preparation of a crystal.
Water content: 0.12%
Lyophilization method: the same as in Example 6.

Example 46

To the liquid preparation (55 mL) produced in the same manner as in Example 7 were added trehalose (1.10 g) and glycine (1.10 g), and a solution (pH 7.8) was obtained. Each vial was filled with the solution (10 mL), lyophilized and then closed airtight to obtain a lyophilized preparation of a crystal.
Water content: 0.03%
Lyophilization method: the same as in Example 7.

Example 47

To the liquid preparation (55 mL) produced in the same manner as in Example 7 were added D-mannitol (0.28 g) and glycine (0.28 g), and a solution (pH 7.9) was obtained. Each vial was filled with the solution (10 mL), lyophilized and then closed airtight to obtain a lyophilized preparation of a crystal.
Water content: 0.07%
Lyophilization method: the same as in Example 6.

Example 48

To the liquid preparation (55 mL) produced in the same manner as in Example 7 were added D-mannitol (1.10 g) and glycine (1.10 g), and a solution (pH 7.8) was obtained. Each vial was filled with the solution (10 mL), lyophilized and then closed airtight to obtain a lyophilized preparation of a crystal.
Water content: 0.04%
Lyophilization method: the same as in Example 7.

Example 49

To the liquid preparation (55 mL) produced in the same manner as in Example 7 were added purified white sugar (1.10 g, manufactured by Ensuiko Sugar Refuting Co., Ltd.) and glycine (1.10 g), and a solution (pH 7.7) was obtained.

Each vial was filled with the solution (10 mL), lyophilized and then closed airtight to obtain a lyophilized preparation of a crystal.
Water content: 0.14%
Lyophilization method: the same as in Example 6.

Example 50

To the liquid preparation (55 mL) produced in the same manner as in Example 7 were added purified white sugar (1.10 g, manufactured by Ensuiko Sugar Refining Co., Ltd.) and glycine (1.10 g), and a solution (pH 7.8) was obtained. Each vial was filled with the solution (10 mL), lyophilized and then closed airtight to obtain a lyophilized preparation of a crystal.
Water content: 0.02%
Lyophilization method: the same as in Example 7.

Example 51

To the liquid preparation (55 mL) produced in the same manner as in Example 41 were added trehalose (0.55 g) and L-alanine (0.55 g), and a solution (pH 7.4) was obtained. Each vial was filled with the solution (10 mL), lyophilized and then closed airtight to obtain a lyophilized preparation of a crystal.
Water content: 0.03%
Lyophilization method: the same as in Example 6.

Example 52

To the liquid preparation (55 mL) produced in the same manner as in Example 7 were added trehalose (0.28 g) and L-alanine (0.28 g), and a solution (pH 7.9) was obtained. Each vial was filled with the solution (10 mL), lyophilized and then closed airtight to obtain a lyophilized preparation of a crystal.
Water content: 0.04%
Lyophilization method: the same as in Example 6.

Example 53

To the liquid preparation (55 mL) produced in the same manner as in Example 7 were added trehalose (0.55 g) and L-alanine (0.55 g), and a solution (pH 7.9) was obtained. Each vial was filled with the solution (10 mL), lyophilized and then closed airtight to obtain a lyophilized preparation of a crystal.
Water content: 0.04%
Lyophilization method: the same as in Example 6.

Example 54

To the liquid preparation (55 mL) produced in the same manner as in Example 7 were added trehalose (1.10 g) and L-alanine (1.10 g), and a solution (pH 7.8) was obtained. Each vial was filled with the solution (10 mL), lyophilized and then closed airtight to obtain a lyophilized preparation of a crystal.
Water content: 0.04%
Lyophilization method: the same as in Example 6.

Example 55

To the liquid preparation (55 mL) produced in the same manner as in Example 42 were added trehalose (0.55 g) and L-alanine (0.55 g), and a solution (pH 8.4) was obtained. Each vial was filled with the solution (10 mL), lyophilized and then closed airtight to obtain a lyophilized preparation of a crystal.
Water content: 0.03%
Lyophilization method: the same as in Example 6.

Example 56

To the liquid preparation (55 mL) produced in the same manner as in Example 7 were added trehalose (0.28 g) and L-alanine (0.28 g), and a solution (pH 8.0) was obtained. Each vial was filled with the solution (10 mL), lyophilized and then closed airtight to obtain a lyophilized preparation of a crystal.
Water content: 0.02%
Lyophilization method: the same as in Example 7.

Example 57

To the liquid preparation (55 mL) produced in the same manner as in Example 41 were added trehalose (0.55 g) and L-alanine (0.55 g), and a solution (pH 7.5) was obtained. Each vial was filled with the solution (10 mL), lyophilized and then closed airtight to obtain a lyophilized preparation of a crystal.
Water content: 0.01%
Lyophilization method: the same as in Example 7.

Example 58

To the liquid preparation (55 mL) produced in the same manner as in Example 42 were added trehalose (0.55 g) and L-alanine (0.55 g), and a solution (pH 8.4) was obtained. Each vial was filled with the solution (10 mL), lyophilized and then closed airtight to obtain a lyophilized preparation of a crystal.
Water content: 0.02%
Lyophilization method: the same as in Example 7.

Example 59

To the liquid preparation (55 mL) produced in the same manner as in Example 7 were added trehalose (1.10 g) and L-alanine (1.10 g), and a solution (pH 7.9) was obtained. Each vial was filled with the solution (10 mL), lyophilized and then closed airtight to obtain a lyophilized preparation of a crystal.
Water content: 0.02%
Lyophilization method: the same as in Example 7.

Example 60

To the liquid preparation (55 mL) produced in the same manner as in Example 7 were added D-sorbitol (0.28 g) and L-alanine (0.28 g), and a solution (pH 7.9) was obtained. Each vial was filled with the solution (10 mL), lyophilized and then closed airtight to obtain a lyophilized preparation of a crystal.
Water content: 0.03%
Lyophilization method: the same as in Example 6.

Example 61

To the liquid preparation (55 mL) produced in the same manner as in Example 7 were added D-sorbitol (0.28 g) and L-alanine (0.28 g), and a solution (pH 7.9) was obtained. Each vial was filled with the solution (10 mL), lyophilized and then closed airtight to obtain a lyophilized preparation of a crystal.
Water content: 0.04%
Lyophilization method: the same as in Example 7.

Example 62

To the liquid preparation (55 mL) produced in the same manner as in Example 7 were added D-mannitol (1.10 g) and L-alanine (1.10 g), and a solution (pH 7.8) was obtained. Each vial was filled with the solution (10 mL), lyophilized and then closed airtight to obtain a lyophilized preparation of a crystal.
Water content: 0.07%
Lyophilization method: the same as in Example 6.

Example 63

To the liquid preparation (55 mL) produced in the same manner as in Example 7 were added D-mannitol (1.10 g) and L-alanine (1.10 g), and a solution (pH 7.8) was obtained. Each vial was filled with the solution (10 mL), lyophilized and then closed airtight to obtain a lyophilized preparation of a crystal.
Water content: 0.04%
Lyophilization method: the same as in Example 7.

Example 64

To the liquid preparation (55 mL) produced in the same manner as in Example 7 were added purified white sugar (0.28 g, manufactured by Ensuiko Sugar Refining Co., Ltd.) and L-alanine (0.28 g), and a solution (pH 7.9) was obtained. Each vial was filled with the solution (10 mL), lyophilized and then closed airtight to obtain a lyophilized preparation of a crystal.
Water content: 0.03%
Lyophilization method: the same as in Example 6.

Example 65

To the liquid preparation (55 mL) produced in the same manner as in Example 7 were added purified white sugar (0.55 g, manufactured by Ensuiko Sugar Refining Co., Ltd.) and L-alanine (0.55 g), and a solution (pH 7.8) was obtained. Each vial was filled with the solution (10 mL), lyophilized and then closed airtight to obtain a lyophilized preparation of a crystal.
Water content: 0.02%
Lyophilization method: the same as in Example 6.

Example 66

To the liquid preparation (55 mL) produced in the same manner as in Example 7 were added purified white sugar (1.10 g, manufactured by Ensuiko Sugar Refining Co., Ltd.) and L-alanine (1.10 g), and a solution (pH 7.8) was obtained. Each vial was filled with the solution (10 mL), lyophilized and then closed airtight to obtain a lyophilized preparation of a crystal.
Water content: 0.03%
Lyophilization method: the same as in Example 6.

Example 67

To the liquid preparation (55 mL) produced in the same manner as in Example 7 were added purified white sugar (0.28 g, manufactured by Ensuiko Sugar Refining Co., Ltd.) and L-alanine (0.28 g), and a solution (pH 7.9) was obtained. Each vial was filled with the solution (10 mL), lyophilized and then closed airtight to obtain a lyophilized preparation of a crystal.
Water content: 0.02%
Lyophilization method: the same as in Example 7.

Example 68

To the liquid preparation (55 mL) produced in the same manner as in Example 7 were added purified white sugar (1.10 g, manufactured by Ensuiko Sugar Refining Co., Ltd.) and L-alanine (1.10 g), and a solution (pH 7.8) was obtained. Each vial was filled with the solution (10 mL), lyophilized and then closed airtight to obtain a lyophilized preparation of a crystal.
Water content: 0.02%
Lyophilization method: the same as in Example 7.

Example 69

To a suspension of Compound A (36.0 g) in Water for Injection (400 mL) was added meglumine (46.2 g), and the mixture was stirred to dissolve Compound A. To the obtained solution was added Water for Injection to give a total volume of 480 mL. Thereafter, the mixture was filtered through a 0.22-μm membrane filter to obtain a liquid preparation (pH 8.6). Each vial was filled with the liquid preparation (8 mL), lyophilized and then closed airtight to obtain a lyophilized preparation of a crystal.
Water content: 0.02%
Lyophilization method: the same as in Example 6.

Comparative Example 1

To a suspension of Compound A (13.8 g) in Water for Injection (50 mL) was added 1 mol/L aqueous sodium hydroxide solution, and the mixture was stirred to dissolve Compound A. Thereafter, 1 mol/L aqueous sodium hydroxide solution was further added to adjust the pH to 8.5. To the solution was added Water for Injection to give a total volume of 161 mL. Thereafter, the mixture was filtered through a 0.22-μm membrane filter to obtain a liquid preparation (pH 8.4). Each vial was filled with the liquid preparation (7 mL), lyophilized and then closed airtight to obtain a lyophilized preparation of an amorphous product.
Water content: 2.2%
Lyophilization Method
1. Vials were cooled at the shelf temperature of −60° C. to freeze the content.
2. The temperature of the vials was increased to the shelf temperature of −10° C. under vacuum (50 Pa or below) and the vials were maintained at the same pressure and the same temperature for 37 hours.
3. The temperature of the vials was increased to the shelf temperature of 0° C. and the vials were maintained at the same pressure and the same temperature for 9 hours.
4. The temperature of the vials was increased to the shelf temperature of 10° C. and the vials were maintained at the same pressure and the same temperature for 4 hours.
5. The temperature of the vials was increased to the shelf temperature of 20° C. and the vials were maintained at the same pressure and the same temperature for 4 hours.
6. The temperature of the vials was increased to the shelf temperature of 40° C. and the vials were maintained at the same pressure and the same temperature for 15 hours.

Comparative Example 2

To a suspension of Compound A (12.0 g) in Water for Injection (70 mL) was added 1 mol/L aqueous sodium hydroxide solution, and the mixture was stirred to dissolve Compound A. Thereafter, 1 mol/L aqueous sodium hydroxide solution was further added to adjust the pH to 8.5. To the solution was added Water for Injection to give a total volume of 160 mL. Thereafter, the mixture was filtered through a 0.22-μm membrane filter to obtain a liquid preparation (pH 8.5). Each vial was filled with the liquid preparation (8 mL), lyophilized and then closed airtight to obtain a lyophilized preparation of an amorphous product.

Lyophilization Method
1. Vials were cooled at the shelf temperature of −60° C. to freeze the content.
2. The temperature of the vials was increased to the shelf temperature of 50° C. under vacuum (50 Pa or below) and the vials were maintained at the same pressure and the same temperature for 39 hours.

Test Example 1

Solubility

To the each vial obtained in Comparative Examples and Examples was added Water for Injection (10 mL) and the vials were shaken by hand. Thus, the dissolution time of the solid substance was measured. The results are shown in Table 3.

TABLE 3

| Example No. | Dissolution time (seconds) |
| --- | --- |
| 2 | 5 |
| 5 | 5 |
| 6 | 18 |
| 7 | 28 |
| 8 | 25 |
| 9 | 18 |
| 10 | 9 |
| 11 | 10 |
| 12 | 18 |
| 13 | 17 |
| 14 | 14 |
| 15 | 9 |
| 16 | 13 |
| 17 | 17 |
| 18 | 16 |
| 19 | 16 |
| 20 | 8 |
| 21 | 18 |
| 22 | 14 |
| 23 | 21 |
| 24 | 9 |
| 25 | 12 |
| 26 | 11 |
| 27 | 20 |
| 28 | 12 |
| 29 | 18 |
| 30 | 8 |
| 31 | 4 |
| 32 | 4 |
| 33 | 5 |
| 34 | 7 |
| 35 | 4 |
| 36 | 3 |
| 37 | 5 |
| 38 | 5 |
| 39 | 8 |
| 40 | 8 |
| 41 | 19 |
| 42 | 10 |
| 43 | 31 |
| 44 | 17 |
| 45 | 9 |
| 46 | 5 |
| 47 | 5 |
| 48 | 13 |
| 49 | 9 |
| 50 | 5 |
| 51 | 5 |
| 52 | 7 |
| 53 | 5 |
| 54 | 5 |
| 55 | 5 |
| 56 | 9 |

TABLE 3-continued

| Example No. | Dissolution time (seconds) |
| --- | --- |
| 57 | 5 |
| 58 | 5 |
| 59 | 7 |
| 60 | 5 |
| 61 | 5 |
| 62 | 5 |
| 63 | 9 |
| 64 | 5 |
| 65 | 5 |
| 66 | 5 |
| 67 | 6 |
| 68 | 8 |
| 69 | 7 |
| Comparative Example 1 | 60 |
| Comparative Example 2 | 65 |

The dissolution time of an amorphous sodium salt (Comparative Example 1) was 60 seconds. The dissolution time of an amorphous sodium salt (Comparative Example 2) was 65 seconds.

The dissolution time of a milled crystal of a meglumine salt monohydrate (Example 2) was 5 seconds. The milled crystal of a meglumine salt exhibited more superior solubility than the amorphous sodium salt.

The dissolution time of an amorphous meglumine salt (Example 5) was 5 seconds. The amorphous meglumine salt exhibited more superior solubility than the amorphous sodium salt.

The dissolution time of preparations (Examples 6 to 9, 41 to 44) produced by lyophilization including an annealing step was 10 to 31 seconds. The preparation produced by this process exhibited more superior solubility than the amorphous sodium salt even though it is not milled.

The dissolution time of preparations (Examples 10 to 13) containing amino acids as an additive; preparations (Examples 14 to 19) containing saccharides as an additive; preparations (Examples 20 to 23) containing sugar alcohols as an additive; preparations (Examples 24 to 26) containing salts as an additive; a preparation (Example 27) containing creatinine as an additive, a preparation (Example 28) containing urea as an additive; a preparation (Example 29) containing nicotinic acid amide as an additive; and a preparation (Example 30) containing trometamol as an additive demonstrate that these preparations exhibit much more superior solubility than an amorphous sodium salt.

Furthermore, the dissolution time of preparations (Examples 31 to 34, 45, 46, 49 to 59, 64 to 68) containing amino acids and saccharides, and preparations (Examples 35 to 40, 47, 60 to 63) containing amino acids and sugar alcohols all fall within the range of 10 seconds and thus exhibited extremely superior solubility.

Test Example 2

Appearance

Appearance was observed. As a result, lyophilized preparations of Examples 7 and 8 looked uniform without a melting mark. Furthermore, the preparations of Examples 12, 15, 27, 31 to 33, 36, 38, 51, 55 and 59 were uniform cakes without a melting mark. The surface of the preparations was smooth and appearance was more satisfactory. Lyophilized preparations having more preferable appearance were obtained by blending additives.

Test Example 3

Stability (1)

The lyophilized preparations of Examples 7, 8, 10, 11, 13, 15, 20, 23, 31, 32, 36 and 40 were allowed to stand still at 40° C. for 6 months and then checked for appearance and residual ratio of Compound A. As a result, appearance change and reduction of the content of Compound A were not observed.

Test Example 4

Stability (2)

The lyophilized preparations of Examples 69 and Comparative Example 1 were irradiated (1,200,000 lx·hr) by a D65 lamp (FLR20S-D-EDL-D65/M) and then their appearance was observed. As a result, appearance change was not observed in the preparation of Example 69; whereas the preparation of Comparative Example 1 turned into orange-yellow.

INDUSTRIAL APPLICABILITY

A preparation filled with a meglumine salt of 6-fluoro-3-hydroxy-2-pyrazinecarboxamide of the present invention is superior in solubility and useful as an injectable preparation.

The invention claimed is:
1. A process for producing a lyophilized preparation comprising a crystal of a meglumine salt of 6-fluoro-3-hydroxy-2-pyrazinecarboxamide, the process comprising:
   (1) cooling an aqueous solution comprising 6-fluoro-3-hydroxy-2-pyrazinecarboxamide and meglumine to produce a frozen product;
   (2) increasing the temperature of the frozen product within the range of −20° C to −5° C.;
   (3) cooling the frozen product again; and
   (4) carrying out lyophilization.

* * * * *